(12) United States Patent
Godbole

(10) Patent No.: US 6,780,289 B2
(45) Date of Patent: Aug. 24, 2004

(54) PROCESS FOR THE PURIFICATION AND RECOVERY OF ACETONITRILE

(75) Inventor: Sanjay P. Godbole, Solon, OH (US)

(73) Assignee: The Standard Oil Company, Warrenville, IL (US)

( * ) Notice: Subject to any disclaimer, the term of this patent is extended or adjusted under 35 U.S.C. 154(b) by 0 days.

(21) Appl. No.: 09/906,299

(22) Filed: Jul. 16, 2001

(65) Prior Publication Data
US 2002/0043455 A1 Apr. 18, 2002

Related U.S. Application Data

(60) Provisional application No. 60/218,865, filed on Jul. 18, 2000.

(51) Int. Cl.$^7$ .............................. B01D 3/14; B01D 3/38; C07C 255/00
(52) U.S. Cl. .............................. 203/79; 203/80; 203/99; 203/DIG. 19; 558/435
(58) Field of Search .............................. 203/73, 79, 80, 203/99, DIG. 19, 78; 558/435

(56) References Cited

U.S. PATENT DOCUMENTS

| | | | | |
|---|---|---|---|---|
| 3,073,753 A | * | 1/1963 | Hadley et al. | 203/81 |
| 3,196,085 A | * | 7/1965 | Dippel | 203/8 |
| 3,870,746 A | * | 3/1975 | Lussling et al. | 558/435 |
| 4,119,497 A | * | 10/1978 | Ocampo et al. | 203/29 |
| 4,294,665 A | * | 10/1981 | Issei et al. | 203/50 |
| 4,362,603 A | * | 12/1982 | Presson et al. | 203/75 |
| 4,859,286 A | * | 8/1989 | Kaibel et al. | 203/75 |
| 5,869,730 A | * | 2/1999 | Graham et al. | 558/320 |
| 6,395,142 B1 | * | 5/2002 | Miles et al. | 203/74 |

FOREIGN PATENT DOCUMENTS

| DE | 3334321 A | 4/1985 |
|---|---|---|
| EP | 0055920 A | 7/1982 |
| EP | 0024788 A | 3/1988 |

OTHER PUBLICATIONS

SU20981 (State Design & Scientific–Research Instituted of the Synthetic Rubber Industry–USSR) Chemical Abstract XP–002185784.

* cited by examiner

Primary Examiner—Virginia Manoharan
(74) Attorney, Agent, or Firm—Thomas E. Nemo

(57) ABSTRACT

A method for the purification of crude acetonitrile comprising distilling the crude acetonitrile in a first fractional distillation column at below atmospheric pressure, withdrawing a first side draw fraction comprising acetonitrile, distilling the first side draw fraction in a second fractional distillation column at super atmospheric pressure, and withdrawing from the second distillation a second side draw fraction comprising purified acetonitrile.

13 Claims, 1 Drawing Sheet

PROCESS FOR THE PURIFICATION AND RECOVERY OF ACETONITRILE

This application claims the benefit of U.S. Provisional Application No. 60/218,865 filed Jul. 18, 2000.

BACKGROUND OF THE INVENTION

This invention is an improved process for the production of acetonitrile. More particularly, this invention is an improved process for the purification of crude acetonitrile produced, for example, as a byproduct during the formation of acrylonitrile by the ammoxidation of an olefin such as propylene or the ammoxidation of propane. This invention is also a process for the purification of recycled and waste solvent acetonitrile.

Acetonitrile is a solvent used in a variety of industrial chemical processes and is a solvent of choice for use in high performance liquid chromatography, usually in combination with one or more solvents such as water or an alcohol. Acetonitrile is also used as a raw material for the preparation of other chemicals used in the chemical and pharmaceutical industry. Pure acetonitrile is desirable for such processes and other uses.

An important source of acetonitrile is a byproduct stream produced during the manufacture of acrylonitrile by the catalytic ammoxidation of propylene such as the process disclosed in U.S. Pat. No. 5,093,299. The catalytic ammoxidation of propylene is a major industrial process and the byproduct stream containing acetonitrile is produced worldwide in hundreds of millions of pounds per year. Although the amounts may vary, a typical example of this byproduct stream contains approximately 50% acetonitrile, 40% water, and smaller amounts of hydrogen cyanide (HCN), acrylonitrile, and other organic materials such as oxazole, allyl alcohol, acetone, and propionitrile. Prior processes for separating the desired acetonitrile from the other components in the byproduct mixture, particularly from water, are not simple. For example, in the process disclosed in U.S. Pat. No. 4,362,603, three different distillation procedures were employed. The first is a high pressure fractional distillation to remove lights and heavies, the second is a low pressure distillation to form an overhead of a water-acetonitrile azeotrope and a heavy fraction which includes water, and the third is a high pressure distillation designed to produce a middle cut or side-draw of relatively pure acetonitrile, a water-acetonitrile overhead and a bottoms or heavy fraction. While this process produces relatively pure acetonitrile, it requires the use of three distillation steps and the attendant recycle streams. The art needs a simpler process for the purification of crude acetonitrile, particularly acetonitrile that is mixed with water or other solvents. The present invention provides such an improved process.

SUMMARY OF THE INVENTION

This invention is a method for the purification of crude or impure acetonitrile comprising distilling the acetonitrile in a fractional distillation column at below atmospheric pressure, withdrawing a first side draw fraction comprising acetonitrile, distilling the first side draw fraction in a second fractional distillation column at super atmospheric pressure, and withdrawing from the second distillation a second side draw fraction comprising purified acetonitrile.

The acetonitrile used in the method of this invention is preferably acetonitrile produced as a byproduct during the ammoxidation of propylene or other suitable hydrocarbon such as propane. However, the method of this invention can be used to purify any source of acetonitrile including, for example, recycle or waste acetonitrile. Such recycle or waste acetonitrile may be acetonitrile that has been used as a solvent in other manufacturing processes, or as a solvent for high pressure liquid chromatography and may contain as impurities various amounts of water and one or more organic impurities.

BRIEF DESCRIPTION OF THE FIGURE

The FIGURE is a schematic representation of one embodiment of the present invention.

DETAILED DESCRIPTION OF THE INVENTION

Figure 1:
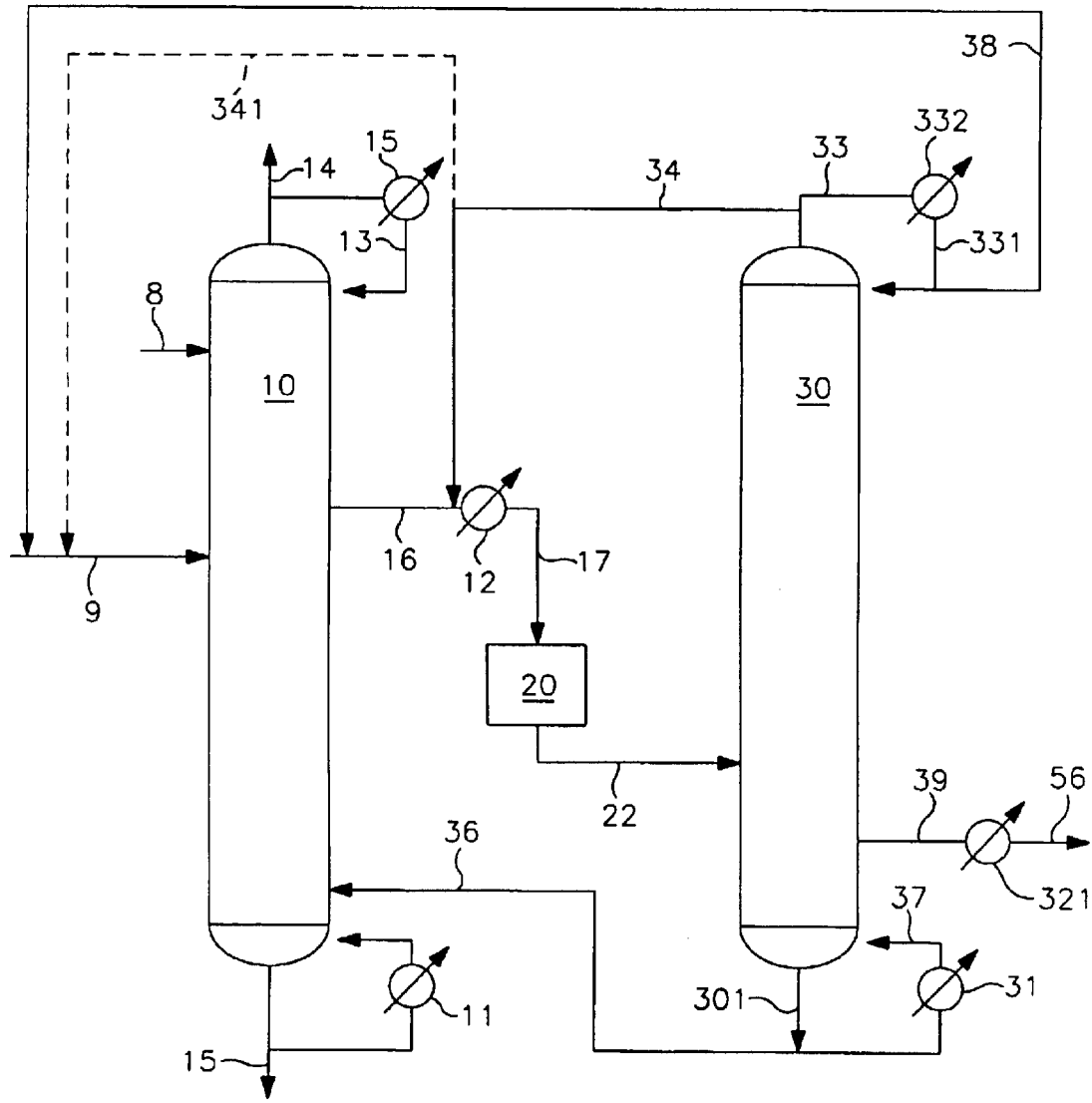

In the method of this invention, a source of crude acetonitrile is treated to produce purified acetonitrile. Purified acetonitrile as used herein means that the acetonitrile is purer, that is, in a greater concentration, than the crude acetonitrile used as the starting material for the purification method. Preferably, purified acetonitrile means acetonitrile that is at least about 95 percent by weight pure, more preferably at least about 98 percent by weight pure and most preferably at least about 99 percent by weight pure. The method of this invention can be used to prepare acetonitrile that is at least about 99.5 percent by weight pure, more preferably at least 99.99 percent by weight pure.

The crude acetonitrile used in the method of this invention can come from any source. However, the method of this invention is most suitable for purifying acetonitrile that is made as a byproduct during the catalytic ammoxidation of a hydrocarbon feed such as propylene or propane by reacting a mixture of, for example, propylene, ammonia and an oxygen-containing gas in the presence of a suitable catalyst. The oxygen-containing gas may, for example, be air, air enriched with pure oxygen gas, or some other form of molecular oxygen. The catalyst is suitably one of a number of catalysts known in the art for the ammoxidation of hydrocarbons such as propylene. Preferable catalysts are those that can operate under the usual molar ratio of air to propylene of at least about 8.5:1. Suitable catalysts are disclosed for example in U.S. Pat. Nos. 3,642,930; 4,485,079; 3,911,089; 4,873,215; 4,877,764; and Japanese Patent Application Nos. 74-87474 and 78-352322.

In such ammoxidation processes, acrylonitrile is produced as the major product. However, smaller amounts of other products such as HCN, acetonitrile, oxazole, allyl alcohol, acetone, and propionitrile are coproduced. Water is also formed. A condensed organic product mixture from the catalytic ammoxidation of propylene typically contains about 10 to about 13 weight percent acrylonitrile, about 16 to about 19 weight percent water, about 0.9 to about 1.5 weight percent HCN, about 0.2 to about 0.4 weight percent acetonitrile and about 1.0 to about 2.0 weight percent other organic compounds including oxazole, allyl alcohol, acetone and propionitrile. Suitable processes for the catalytic ammoxidation of propylene to acrylonitrile are disclosed in U.S. Pat. Nos. 5,093,299; 4,863,891; 4,767,878; and 4,503,001, all of which are hereby incorporated by reference in their entirety.

After the ammoxidation reaction, it is necessary to isolate the desired acrylonitrile, acetonitrile and HCN products from the reactor effluent. In a typical process, the effluent is treated to remove residual ammonia. The remaining mixture is suitably treated by a number of distillation processes to isolate the desired acrylonitrile. During this purification process, a product stream rich in acetonitrile is produced. It is this stream rich in acetonitrile that is highly suitable for use in the method of this invention to make purified acetonitrile. Such an acetonitrile rich stream may contain about 30 to about 78 weight percent acetonitrile, about 20 to about 68 weight percent water, about 0.01 to about 10 weight percent HCN, and about 1.0 to about 5.0 weight percent of other organics such as, for example, oxazole, allyl alcohol, acetone, and acrylonitrile. Processes for the purification of acrylonitrile are, for example, set forth in U.S. Pat. Nos. 4,234,501; 3,885,928; 3,352,764; 3,198,750; and 3,044,966, which are hereby incorporated by reference in their entirety.

In addition to purifying the crude acetonitrile recovered during the manufacture of acrylonitrile by the ammoxidation of propylene or other hydrocarbons, the method of this invention can be used to manufacture purified acetonitrile from recycled streams or waste streams containing acetonitrile. Such recycle streams, for example, can come from some other chemical process where acetonitrile is used as a solvent or as a starting material for the manufacture of other chemical compositions. Such recycle streams are also produced by high pressure liquid chromatography procedures. The acetonitrile, usually in combination with one or more cosolvents such as water or an alcohol such as methanol, ethanol or isopropyl alcohol, is used as the mobile phase in high performance liquid chromatography. Such procedures produce a waste stream of acetonitrile contaminated with low amounts of various chemical compounds, typically much less than 0.1 weight percent, but containing relatively large amounts, typically about 10 to about 80 weight percent, of one or more cosolvents used in the chromatographic procedure. Thus, as used herein, recycle acetonitrile means a source of acetonitrile that has been recovered from at least one chemical, analytical or other procedure and which contains at least one impurity. Typical impurities may include one or more of, for example, water, methanol, ethanol, isopropanol, allyl alcohol, isopropyl acetate, one or more heptanes, trimethyl silanol, hexamethyl disiloxane, benzene and tetrahydrofuran. The amount of the impurity or impurities is generally about 0.01 weight percent to about 80 weight percent based on the weight of the mixture, however, the amount of impurities in the recycle acetonitrile is usually less than about 25 weight percent with no single component greater than about 10 weight percent, based on the weight of the mixture.

In the preferred process of this invention, the crude acetonitrile is first distilled in a first distillation column at below atmospheric pressure to remove light components and heavy components, typically water, by removing an acetonitrile-containing first side draw stream for further processing. By side draw it is meant that the acetonitrile-containing stream is taken from a point between the top and the bottom of the column. Such a side draw can be taken at a location below the location where the feed enters the column if the feed has a relatively high level of light, lower boiling impurities, or it can be taken at a point above the location where the feed enters the column if the feed has a relatively high level of heavy impurities. Preferably, the side draw is located in the middle 80 percent of the column, more preferably in the middle 66 percent of the column.

The first side draw stream is directed to a second distillation column where it is again distilled. A second side draw stream of purified acetonitrile is removed from the second column. Prior to the second distillation, the first side draw stream can be treated to remove impurities which were not removed in the first distillation. For example, a chemical treatment can be employed to eliminate one or more impurities. When the crude acetonitrile being treated by the method of this invention is acetonitrile produced as a byproduct from the manufacture of acrylonitrile by the ammoxidation of propylene, the crude acetonitrile stream, as mentioned above, usually contains hydrogen cyanide (HCN), for example, about 0.01 up to about 10 weight percent HCN. If the crude acetonitrile stream contains HCN, a portion of this HCN can be removed from the acetonitrile stream as a light end in the first distillation column. Nevertheless, some of the HCN may remain in the first side draw. The HCN in the first side draw can be removed conveniently by any suitable means for removing HCN from an aqueous acetonitrile feed stream. For example, it can be treated with a base such as sodium hydroxide, with an aldehyde such as formaldehyde, with ozone, or iron salts. However, since a subsequent step in the process preferably does not utilize a distillation column having a bottom fraction containing water, it is preferable not to use a reagent for removing the HCN which either forms or has a salt as a byproduct. As an alternative, the crude acetonitrile can be treated prior to the first distillation column by a digestion process such as that described in U.S. Pat. No. 4,328,075, which is hereby incorporated by reference in its entirety. In that digestion process, the crude acetonitrile stream containing the HCN is reacted with a solution of caustic, for example sodium hydroxide, and an aldehyde, for example formaldehyde, to remove the HCN. As another alternative, the digester as disclosed in U.S. Pat. No. 4,328,075 can be used after the first distillation of this invention if an additional distillation column, either atmospheric or subatmospheric, to remove the reagents used by or products formed in such a digestion step. This would be particularly useful where there is an appreciable amount of HCN or acrylonitrile present in the first distillation column.

The use of a vacuum column as a first column in accordance with this invention unexpectedly reduces hydrogen cyanide polymerization in the first column. The reduction in polymerized HCN provides for reduced fouling of the upper portion of the column and overhead apparatus thus increasing the time the column can be used before removal of the polymerized HCN is required. The use of a vacuum column also decreases the amounts of heavy components carried downstream in the purification process. This results in a superior acetonitrile product particularly because the resulting product has fewer components that absorb in the ultraviolet range. It also reduces the amount of water as early as possible in the purification process thereby reducing the amount of material to be recycled.

The process of this invention for the purification of crude acetonitrile will be described in greater detail using crude acetonitrile obtained from the manufacture of acrylonitrile by the ammoxidation of propylene as described hereinabove. However, it is to be understood that using such crude acetonitrile is only an embodiment of the present invention and the processing conditions, processing steps, equipment and other elements of this embodiment can be used for the purification of other sources of impure acetonitrile including recycle or waste acetonitrile, or mixtures of recycle or waste acetonitrile with acetonitrile obtained from other sources such as crude acetonitrile obtained as a byproduct from the manufacture of acrylonitrile by the ammoxidation of propylene or other hydrocarbons.

Crude acetonitrile in the form of a mixture comprising about 30 to about 78 weight percent acetonitrile, about 20 to about 68 weight percent water, about 0.01 to about 10 weight percent HCN and about 0.1 to about 5 weight percent other organic compounds such as oxazole, allyl alcohol, acetone, and acrylonitrile is distilled in a first fractionation column at a top column pressure suitably about 1.5 to about 14 psia, preferably about 2.5 to about 10 psia, and most preferably about 3.5 to about 5.0 psia. The distillation is conducted so that a lower, preferably bottom stream is withdrawn containing the heavy components in the crude acetonitrile, and an upper, preferably overhead stream containing the light components. Heavy components are those components having a boiling point greater than acetonitrile or the acetonitrile-water azeotrope at the pressure used to operate the column. Water is the major heavy component. Light components are those components having a boiling point lower than the boiling point of acetonitrile or the acetonitrile-water azeotrope at the pressure used for the distillation. HCN is a light component as well as, for example, oxazole, acrolein, and acrylonitrile. A side stream or side draw is removed from the distillation column. Depending on the temperature and pressure selected for the first distillation, as well as the location on the column where the side stream is taken, this side draw comprises acetonitrile and water and other impurities, however, it is rich in acetonitrile compared to the crude acetonitrile stream. For example, the distillation is conducted so that the azeotropic side draw stream suitably comprises about 82 to about 90 weight percent acetonitrile and about 8 to about 16 weight percent water, preferably about 86 to about 89 weight percent acetonitrile and about 9 to about 17 weight percent water. If the side draw is taken at a point on the column above where the feed is added, the side draw stream is preferably taken as a liquid because the vapor phase is richer in light components. If the side draw is taken below the feed, the side draw stream is preferably taken as a gas because the liquid is richer in heavy components.

The first distillation column preferably has a reflux loop located at the upper portion of the column at a point above where the first side draw is located, preferably at the top of the column. Thus, a portion or the upper fraction of the column, preferably the top fraction, is returned to the column as reflux. The reflux ratio, which is the weight ratio of the amount of upper or top fraction returned to the column divided by the amount of overhead or upper fraction of the column removed from the column, is suitably about 1 to about 50, more preferably about 20 to about 30. The upper or overhead fraction not returned as reflux can be condensed. At least a portion of the condensate can be directed back to the acrylonitrile purification process as a recycle stream. Preferably, it is recycled to one of the acrylonitrile product distillation columns used for isolating acrylonitrile. Most preferably, it is the column which can be used to supply the crude acetonitrile stream useful as a feed material in the method of this invention. The reflux is preferably returned to the first distillation column at a point above the first side draw. Most preferably, at the top of the column. The portion of the upper or overhead fraction that is not condensed is preferably disposed of by, for example, incineration.

The first distillation column may have packing or plates to assist with the distillation of the crude acetonitrile. If it has plates, the plates can be sieve, trays or bubble cap and the like. The number of theoretical plates is preferably about 25 to about 40.

In a preferred embodiment, water, in addition to the water contained with the crude acetonitrile, can be added to the first distillation column. The water, if added, is preferably added to the upper portion of the column above a point where the side draw is taken and below where the upper or top fraction is removed. The water is added to assist further with the distillation and provide for an extractive distillation of the impurities in the crude acetonitrile such as acrylonitrile and methyl acetate, if present, which is removed in the overheads. The amount of water added is an amount that provides for the purification of the crude acetonitrile to the desired level. However, generally, the amount of water added is such that the weight ratio of water added to acetonitrile present in the crude acetonitrile is about 0.1:1 to about 10:1, and more preferably about 0.2:1 to about 5:1.

The first side draw stream may also comprise smaller amounts of impurities such as HCN which were not removed as either lights or heavies. For example, as described above, it may contain about 0.01 to about 0.5 weight percent HCN, or about 0.05 to about 0.1 weight percent HCN. These impurities, particularly the HCN, are preferably removed, for example, by subjecting the acetonitrile stream to a treatment with a chemical reagent or reagents as described above that can react with and remove the HCN from the stream such as an aldehyde like formaldehyde, a caustic such as sodium hydroxide or one or more iron salts.

The first side draw stream, optionally after subjecting it to the digestion process described above or to some other process or processes to remove residual impurities, is directed to a second distillation column to be purified further. The first side draw stream is distilled in the second fractionation column at a top pressure of about 30 to about 120 psia, preferably about 60 to about 100 psia, and most preferably about 85 to about 90 psia. The distillation is conducted so that a lower, preferably bottom stream is withdrawn containing the heavy components, and an upper, preferably top stream is withdrawn containing the light component. Heavy components are those components having a boiling point higher than acetonitrile. Light components include the components having a boiling point lower than the boiling point of acetonitrile and azeotropes such as the water-acetonitrile azeotrope. A side stream or side draw is removed from the second distillation column. Preferably, the side draw is located in the middle 80 percent of the column, more preferably in the middle 66 percent of the column. This second draw stream is the purified acetonitrile according to the method of this invention. The product side draw can be a liquid or vapor taken, preferably, below the feed stream entry point on the column.

The second distillation preferably has a reflux loop located at the upper portion of the column at a point above the second side draw, preferably at the top of the column. Thus, at least a portion or the upper fraction of the column, preferably the top fraction, is returned to the column as reflux. The reflux ratio for the second distillation column, which is the weight ratio of the amount of upper or top fraction returned to the column divided by the amount of total overhead draw removed from the column, is suitably greater than about 3, preferably about 3 to about 10, more preferably about 5 to about 8. The upper or top fraction can be withdrawn as a liquid or combination of liquid and vapor. The liquid draw is preferably directed as a feed to the first column, i.e., the light ends drying column, preferably above the first draw point. The vapor, if present, is preferably recycled to the second column preferably by mixing it with the side draw from the first column. The reflux in the second distillation column is preferably returned to the second distillation column at a point above the second draw. Preferably, the second distillation column has packing or plates to assist with the distillation of the acetonitrile. If it has plates, the plates can be sieve, trays or bubble cap and the like. The number of theoretical plates is preferably about 20 to about 30. A purified acetonitrile product is withdrawn from the second column as a side draw suitably below the point where the feed enters the second column. The purified acetonitrile is preferably at least about 99 weight percent pure, more preferably at least about 99.8 weight percent pure, and most preferably at least about 99.99 weight percent pure. If desired, this acetonitrile stream can be subjected to further purification to remove, for example, any minor impurities that may, for example, absorb in the ultraviolet.

DETAILED DESCRIPTION OF THE FIGURE

A preferred embodiment of the present invention will now be described with reference to the attached FIGURE.

Acetonitrile feed, either crude acetonitrile, recycle acetonitrile or a combination thereof is fed via inlet line 9 and water via inlet line 8, or optionally via line 13, is fed to the first fractional distillation column, also called the light ends drying column, 10 wherein the acetonitrile feed and water are distilled at a pressure of about 2.5 to about 5.0 psia. The distillation is conducted at a rate so as to allow most and preferably all of any light impurities in the acetonitrile feed to be removed through the light end overhead line 14. The impurities present are extractively distilled by the water fed to column 10. In addition, a stream comprising acetonitrile containing a small amount of heavy impurities is also charged into the light ends drying column 10 via line 36 from product column 30. An acetonitrile-water azeotrope rich in the lights from the product column 30 enters the light ends column feed via line 34. The light impurities (e.g. isopropyl acetate, acrylonitrile, oxazole) in the waste solvent or crude acetonitrile feed, either due to their low boiling points or aided by extractive distillation in the presence of water, are also withdrawn from column 10 as a vapor draw in line 14 and partly refluxed back into the upper region of column 10 via reflux condenser 15 and reflux line 13. Preferably, the reflux ratio is about 25:1. Unrecovered overheads are removed through line 14 and transported to vent scrubbers or condensers (not shown) for waste treatment. Water is recovered from the bottom of light ends column 10 and discharged via line 15 to waste treatment with partial recycle through reboiler 11. A first acetonitrile/water azeotrope containing about 88% acetonitrile, about 10% water, about 1000 ppm HCN, less than 10 ppm volatile lights and any heavy organics is recovered via line 16 as a vapor side draw, condensed in condenser 12 and transported via line 17 to an optional treatment unit 20 for the removal of any HCN or acrylonitrile, if present. Remainder of water and most of the heavies leave column 10 through line 15 and are directed to waste disposal.

In one embodiment, a liquid side draw can be taken if most of the impurities were light impurities. In another configuration, the location of the side draw could be below the feed tray location.

If there are no significant impurities such as HCN and acrylonitrile to be removed after the first distillation, no treatment unit 20 is required. Alternatively, an HCN removal unit such as the digester described in U.S. Pat. No. 4,328,075, can be used to remove HCN before crude acetonitrile feed enters the first distillation column.

The HCN-free acetonitrile and water mixture passing out of treatment unit 20 is charged via line 22 into a product column 30 and is distilled at high pressure, e.g. 50 psia, into top, middle and bottom fractions. A fraction comprising acetonitrile containing heavy impurities is withdrawn from the bottom of product column 30 via line 301 into reboiler 31 for partial recycling to column 30 via line 37 and light ends drying column 10 via line 36. A second acetonitrile/water azeotrope is withdrawn from the top of product column 30 and condensed and recycled as reflux back to the top of product column 30 via lines 33, 331 and reflux condenser 332. Part of the condensed liquid can be recycled back to column 10 through line 38. The uncondensed vapors continue via line 34 to the azeotrope condenser 12 where they are mixed with the first azeotrope from line 16. Alternatively, these uncondensed vapors may be rerouted to light ends drying column 10 via lines 34 and 341. Preferably, the reflux ratio as defined above is about 5:1 for this step of the process. Because product column 30 is operated at high pressure, water in the second acetonitrile/water azeotrope charged into product column 30 is recovered in the overhead stream of product column 30, i.e. the second acetonitrile/water azeotrope, leaving high purity acetonitrile in the product column. This high purity acetonitrile (99.99 wt % acetonitrile) is drawn off column 30 as a sidestream via line 39 (this stream may be a vapor or liquid, preferably a vapor), and, after cooling in heat exchanger 321, is discharged via line 56 into an optional resin treatment bed such as that described in EP 890572 A1.

The above description is not intended to be exhaustive or limiting as to the description of the present invention, but merely as illustrative of the practice of the process of the present invention. It is evident that many alternatives, modifications and variations will be apparent to those skilled in the art in light of the foregoing description. Accordingly, it is intended to embrace all such alternatives, modifications and variations as fall within the spirit and broad scope of the appended claims.

EXAMPLE

A first distillation column containing 60 actual trays (50% efficiency) is equipped with an overhead condenser, and a reboiler. A second distillation column containing 57 actual trays (50% efficiency) is equipped with an overhead condenser and a reboiler. The operating pressures for the first column and the second are 3.0–9.0 Psia. and 85–90 Psia., respectively. Solvent water at a rate of about 1 gallon per minute (GPM) at 90° F. was introduced at the top tray of the first column. A crude acetonitrile stream (9.0 GPM) having the composition of 66 wt % acetonitrile, 28.8 wt % water, 2.5 wt % HCN, 800 part per million by weight (PPM) acrylonitrile, 1.3 wt % propionitrile, 1.2 wt % oxazole, and other trace impurities is fed at 75° F. to the first distillation column (operated under reduced pressure stated above) at tray 40 at a rate of 9.0 GPM. The reflux ratio for the first column is maintained at 30.

A liquid side-draw of 3970 lb/hr is withdrawn from tray 24 of the first distillation column and introduced on tray 16 to the second column (operated at the elevated pressure stated above). The reflux ratio for the first column is maintained at 6.8. A vapor side-draw of 1938 lb/hr, taken from tray 38 of the second column, is 99.95 wt % acetonitrile, with less than 600 PPM propionitrile and less than 5 PPM oxazole.

The above description is not intended to be exhaustive or limiting as to the description of the present invention, but merely as illustrative of the practice of the process of the present invention. It is evident that many alternatives, modifications and variations will be apparent to those of skill in the art.

U.S. Provisional Application No. 60/218,865 filed Jul. 18, 2000 is hereby incorporated by reference in its entirety.

That which is claimed is:

1. A method for the purification of crude acetonitrile comprising distilling the crude acetonitrile in a first fractional distillation column at below atmospheric pressure, withdrawing a first side draw fraction comprising acetonitrile, distilling the first side draw fraction in a second fractional distillation column at super atmospheric pressure, and withdrawing from the second distillation a second side draw fraction comprising purified acetonitrile.

2. The method of claim 1 wherein the crude acetonitrile comprises crude acetonitrile produced by the catalytic ammoxidation of propylene or propane.

3. The method of claim 1 wherein the crude acetonitrile comprises waste acetonitrile.

4. The method of claim 1 wherein the crude acetonitrile comprises about 38 to 78 weight percent acetonitrile, about 20 to about 68 weight percent water, and about 0.01 to about 10 weight percent HCN.

5. The method of claim 1 wherein the pressure in the first fractional distillation column is about 1.5 to about 14 psia.

6. The method of claim 1 wherein the pressure in the second fractional distillation column is about 30 to about 120 psia.

7. The method of claim 1 wherein the crude acetonitrile comprises water and wherein the first side draw fraction comprises about 82 to about 90 weight percent acetonitrile and about 8 to about 16 weight percent water.

8. The method of claim 1 wherein the crude acetonitrile comprises HCN and wherein the first side draw fraction further comprises HCN and is treated to reduce the amount of HCN contained therein prior to distilling the first side draw fraction in the second distillation column.

9. The method of claim 1 wherein the crude acetonitrile comprises HCN and is treated to remove HCN prior to distillation in the first fractional distillation column.

10. The method of claim 1 wherein the purified acetonitrile is at least 99 weight percent pure.

11. The method of claim 1 wherein water is added to the first fractional distillation column.

12. The method of claim 11 wherein the water is added to the first fractional distillation column above where the first side draw fraction is withdrawn.

13. The method of claim 11 wherein the amount of water added is such that the weight ratio of water added to acetonitrile present in the crude acetonitrile is about 0.1:1 to about 10:1.

* * * * *